US006432129B2

(12) United States Patent
DiCaprio

(10) Patent No.: US 6,432,129 B2
(45) Date of Patent: Aug. 13, 2002

(54) STENT DELIVERY SYSTEM

(75) Inventor: Fernando DiCaprio, Mendota Heights, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/510,427

(22) Filed: Feb. 22, 2000

(51) Int. Cl.$^7$ .................................................. A61F 2/06
(52) U.S. Cl. ...................................................... 623/1.11
(58) Field of Search ................................ 606/108, 194, 606/195, 192, 198, 191; 623/1.11; 604/102.01, 103.04, 103.11, 96.01

(56) References Cited

U.S. PATENT DOCUMENTS

| | | | |
|---|---|---|---|
| 4,444,188 A | * 4/1984 | Bazell et al. | 604/103.04 |
| 4,950,227 A | 8/1990 | Savin et al. | 604/8 |
| 5,108,416 A | * 4/1992 | Ryan et al. | 606/194 |
| 5,403,341 A | 4/1995 | Solar | 606/198 |
| 5,653,736 A | 8/1997 | Glastra | 606/198 |
| 5,772,674 A | * 6/1998 | Nakhjavan | 606/194 |
| 5,810,871 A | * 9/1998 | Tuckey et al. | 606/108 |

FOREIGN PATENT DOCUMENTS

WO          9603092          2/1996

* cited by examiner

Primary Examiner—Kevin T. Truong
(74) Attorney, Agent, or Firm—Vidas, Arrett & Steinkraus P.A.

(57) ABSTRACT

A stent delivery system comprising a catheter, an inflatable portion, a stent, and a pair of stent retaining sleeves. The inflatable portion having ends which are rounded in shape providing a hemispherical contour. The inflatable portion further being characterized as having a non-inflated state and an inflated state. The pair of stent retaining sleeves having first portions which overlie the ends of the inflatable portion and are shaped to correspond to the contour of the ends of the inflatable portion. The pair of stent retaining sleeves having second portions which are attached to the catheter. The stent disposed about the inflatable portion, and having margins. The first portions of the sleeves at least partially overlying the margins of the stent when the inflatable portion is in the non-inflated state. The stent being released from the sleeves when the inflatable portion is inflated to the inflated state.

13 Claims, 2 Drawing Sheets

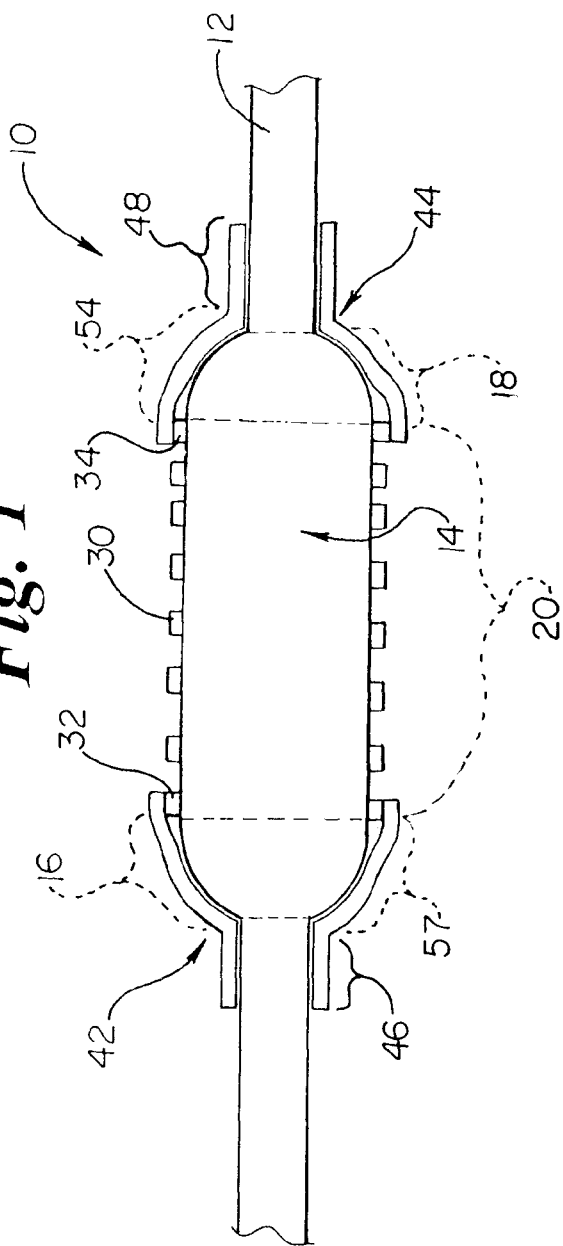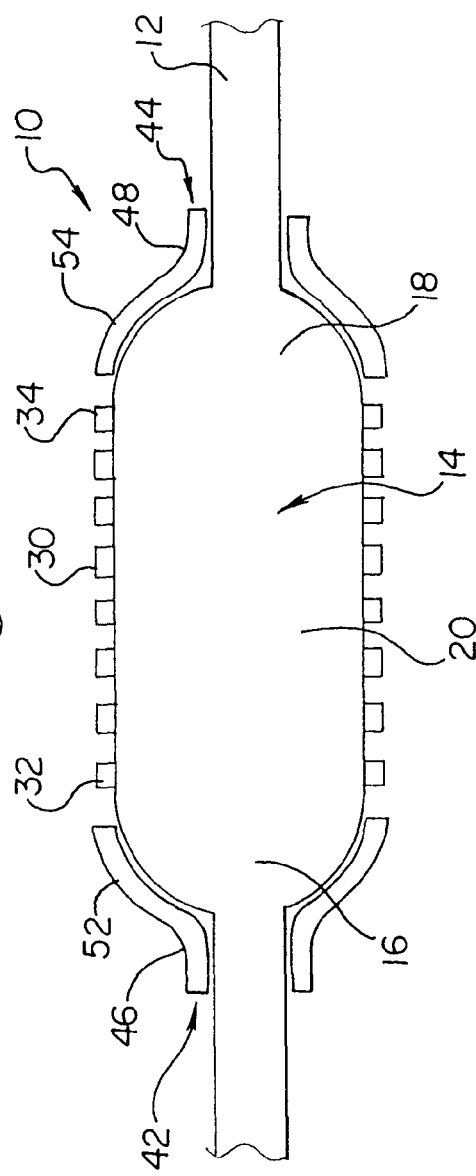

STENT DELIVERY SYSTEM

BACKGROUND OF THE INVENTION

The patent relates to a delivery system in which a catheter carries a stent on its distal end portion. The stent may be held in place around the catheter prior to and during percutaneous delivery by means of one and preferably two end sleeves, or the stent may be crimped to hold it in place. The stent may be self-expanding, such as a NITINOL shape memory stent, or it may be expandable by means of an inflatable portion of the catheter, such as a balloon. The inflatable portion or balloon is configured to have rounded ends, with the end sleeves overlying the ends of the balloon and shaped correspondingly.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under positive external pressure in order to maintain their reduced diameter configuration during delivery of the stent to its deployment site. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with delivery and deployment of inflation expandable stents, although it is generally applicable to self-expanding stents when used with balloon catheters.

An example is the stent described in PCT Application NO. 960 3092 A1, published Feb. 8, 1996, the content of which is incorporated herein by reference.

In advancing an inflation expandable stent through a body vessel to the deployment site, there are a number of important considerations. The stent must be able to securely maintain its axial position on the delivery catheter without translocating proximally or distally and especially without becoming separated from the catheter. The stent, particularly its distal and proximal ends, must be protected to prevent distortion of the stent and to prevent abrasion and/or reduce trauma of the vessel walls.

Inflation expandable stent delivery and deployment assemblies are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site. The content of all of these patents is incorporated herein by reference.

In previous inflatable stent delivery systems which utilize an inflatable portion (balloon, etc) to deliver the stent, the balloon is constructed and arranged to include a stent mounting region located between two end cones. The design of such a balloon usually has end cones oriented in a standard uniform 45 degree angular cone extending from the catheter shaft to the stent mounting region of the balloon. A prior stent delivery catheter having a balloon with cone shaped ends is shown in FIG. 4.

The end cone shape described above, provides the ends of a stent delivery balloon with expansion characteristics which are well known to those of ordinary skill in the art and described in greater detail below. However, a balloon having such cone shaped ends may not be ideal for use with a stent delivery system which utilizes socks, sheathes or sleeves as shown in FIG. 1 to retain the stent on the balloon.

When such a balloon with cone shaped ends is utilized in a stent delivery system having retaining socks, sheathes, or sleeves, as described above, the sleeves may not uniformly release the stent or the stent may fail to release at all when the balloon is inflated under low pressure, such as a pressure value between approximately 4 to 10 ATM. The failure to release the stent is due to an insufficient increase in length of the cone shaped ends when the balloon is inflated under low pressure. While it may be possible to use higher pressure, such as a pressure value between approximately 10 to 18 ATM to further expand the balloon ends, this may be undesirable as such increased pressure may cause the balloon and/or vessel to distort or rupture.

The present invention overcomes these problems by providing an inflatable portion, balloon or other type of expandable device, which has rounded ends as opposed to the more common cone shaped ends described above. Relative to the 45 degree angle oriented cone shaped ends of previous balloons, the rounded ends of the present balloon provide additional length to the balloon when it is inflated. As a result the present stent delivery system has improved capability to more effectively remove the sleeves, socks, etc from the stent.

In order to safely and effectively advance a stent delivery catheter through the tortious and narrow confines of various bodily vessels, it is well known that it is desirable to have a stent delivery system with a reduced profile prior to delivery of the stent. However, in order to remove the catheter from the body and minimize damage to any bodily vessels through which the catheter may be drawn, it is also desirable to provide a stent delivery system with a reduced profile subsequent to stent delivery.

To provide the balloon with a reduced profile subsequent to stent delivery, most prior stent delivery systems rely on deflation of the balloon, by simply drawing inflation fluid from the catheter. This method is insufficient, as the balloon may remain in a somewhat enlarged and/or distorted state even after removal of all inflation fluid. As a result of this shortcoming, it would be advantageous to provide a stent delivery system which has a balloon that could be collapsed more effectively. This would provide the catheter with the desirable post stent delivery low profile, allowing the catheter to be safely and readily withdrawal from a bodily vessel and the deployed stent and into the guiding catheter. The present invention provides such a stent delivery system and is described below.

BRIEF SUMMARY OF THE INVENTION

The present invention provides a stent delivery system having an inflatable portion or balloon which has rounded ends rather than the more common conical shaped ends. Balloon ends which are rounded provide increased end length when the balloon is inflated. Depending on the precise shape of other rounded balloon ends varying end length increases will be provided for. Preferably, the present balloon ends are hemispherical.

The hemispherical ends of the balloon provide at least an 11 percent increase in end length when the balloon is inflated under low pressure between approximately 4 to 10 ATM. This increase in end length is in comparison to a similar balloon of like material, inflated under the same pressure, but having coned shape or conical ends, where the conical ends are uniformly disposed about the longitudinal axis of the catheter at an angle of approximately 45 degrees. The increased length of the rounded balloon ends in the inflated state, provides the present invention with superior ability to retract the retaining sleeves from the stent margins when the balloon is inflated to low pressure.

The present invention includes retaining sleeves which overlie the rounded ends of the balloon. Subsequent to stent delivery and deflation of the balloon, the rounded balloon ends and the correspondingly shaped retaining sleeves cooperatively function to compress the balloon ends. This feature provides the balloon with a more collapsed configuration than the balloon would otherwise have relying on deflation alone, and provides the delivery catheter with the desired low profile for withdrawal as described above.

In addition, the unique configuration of the balloon ends and retaining sleeves of the present invention, provides an improvement over the prior art by providing a stent delivery system which requires no lubrication between the balloon or stent surfaces, and the inside surfaces of the retaining sleeves.

BRIEF DESCRIPTION OF THE SEVERAL VIEWS OF THE DRAWINGS

A detailed description of the invention is hereafter described with specific reference being made to the drawings in which:

FIG. 1 is a side perspective view of the present stent delivery system shown prior to stent delivery;

FIG. 2 is a side perspective view of the present stent delivery system shown with the inflatable portion in the inflated state during stent delivery.

DETAILED DESCRIPTION OF THE INVENTION

Figure 3:
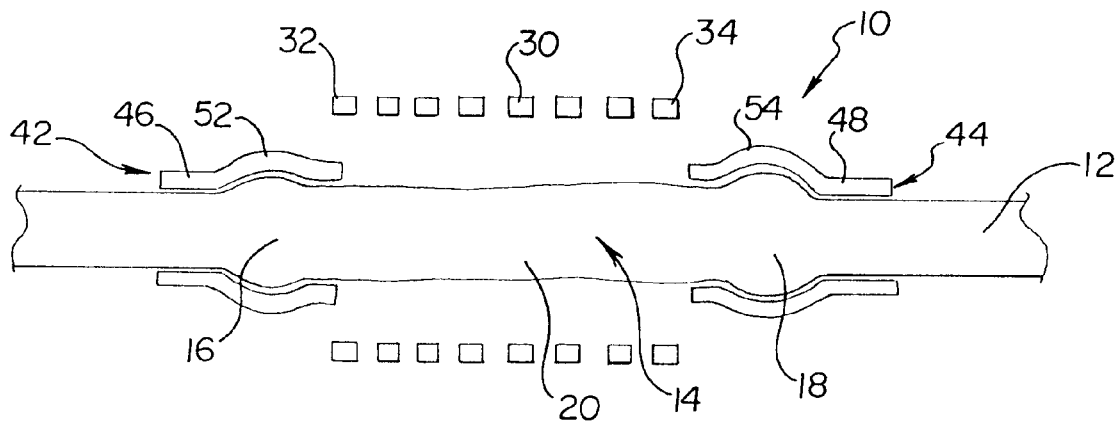
FIG. 3 is a side perspective view of the present stent delivery system shown subsequent to stent delivery and deflation of the inflatable portion.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

FIG. 1 shows an embodiment of the present stent delivery system. In the embodiment shown a stent delivery catheter, indicated generally at 10, includes an elongated shaft 12 having an inflatable portion 14. In an alternative embodiment the inflatable portion may be a balloon or other inflatable device separate from the catheter shaft. In such an embodiment the balloon may be attached to the catheter shaft using retaining rings disposed about the ends of the balloon, bonding or welding the balloon to the catheter shaft, or otherwise attaching the balloon and the catheter shaft together. In all embodiments the inflatable portion or balloon may be composed of any thermoplastic polymer or polymers, alone or in combination, in single or multiple layers.

For purposes of description, inflatable portion 14 is divided into three portions: a proximal end 16, a distal end 18 and an elongated body portion 20 which defines the area of the balloon which is between the proximal and distal ends. As previously mentioned, the ends of the balloon have a rounded construction. In the more preferred embodiment shown in FIGS. 1–3, proximal end 16 and distal end 18 are hemispherical in shape.

When the inflatable portion placed in the inflated state as shown in FIG. 2, the hemispherical shape of the balloon ends provide an increased length to the ends of at least 11 percent, when compared to a similar balloon equipped with conical ends. The increased length of the rounded ends is best explained by an understanding of FIGS. 4 and 5.

Figure 4:
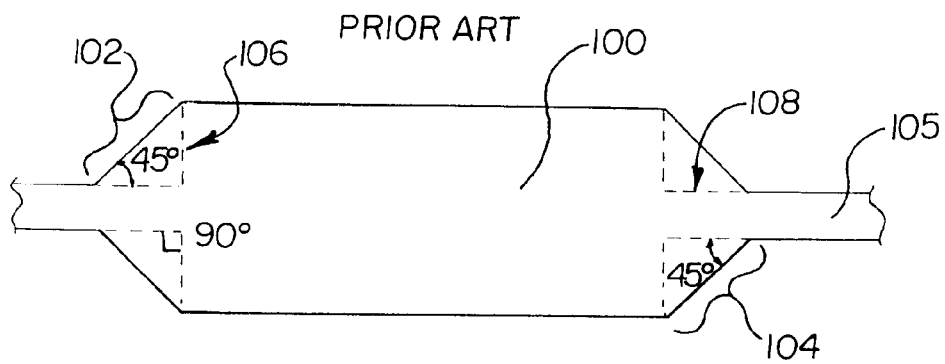
FIG. 4 is a side perspective view of a prior art balloon having cone shaped ends of 45 degree orientation.

FIG. 4 shows a standard prior art balloon 100, in the inflated state, equipped with ends 102, 104 which are cone shaped. The balloon shown has a catheter shaft 105. The cone ends 102, 104 form a 45 degree angle with the catheter shaft as shown. Vertical base lines 106, and horizontal base lines 108 form a 90 degree angle at their intersection and are depicted in order to illustrate that an equilateral triangle is formed between a given vertical base line, horizontal base line, and the hypotenuse (i.e. each surface of the cone shaped ends 102, 104 ). If both vertical base lines 106 and horizontal base lines 108 are all given a theoretical length of 1 mm, then as a function of the Pythagorean theorem the respective surfaces of the cone shaped ends 102, 104 will have a length equivalent to the square root of 2 mm. The formula and application are as follows:

$$\text{ConeLength}^2 = 1\text{ mm}^{2*} + 1\text{ mm}^2 = 2\text{ mm}$$

$$\text{ConeLength} = \sqrt{2\text{ mm}}$$

*Assume vertical base and horizontal base lengths respectively=1 mm

Figure 5:
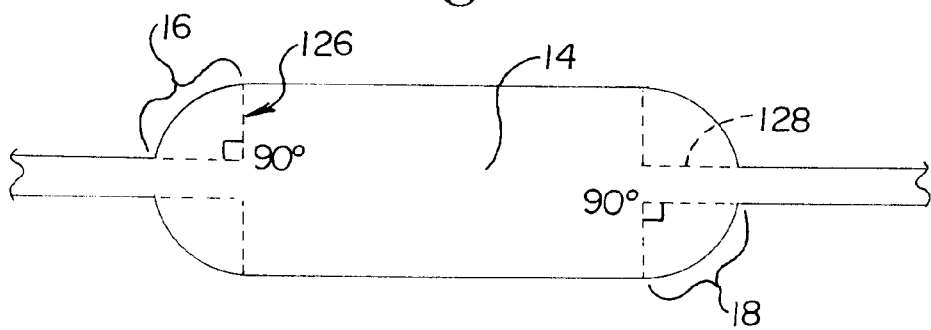
FIG. 5 is a side perspective view of a balloon having hemispherical ends.

Turning to FIG. 5, the inflatable portion or balloon 14, as used in the present stent delivery system is shown. As can be seen, balloon 14 has proximal and distal hemispherical shaped ends 16, 18. As in FIG. 4 vertical base lines 126 and horizontal base lines 128 are given a theoretical length of 1 mm. Vertical base lines 126, and horizontal base lines 128 form a 90 degree angle at their intersection and are depicted in order to illustrate that an quarter of a circle is formed between a given vertical base line, horizontal base line, and each surface of the cone shaped ends 16, 18. Because the ends 16, 18 are hemispherical in shape, and the area contained by each of the vertical base lines, horizontal base lines and end surfaces forms a quarter circle, the length of each surface of the ends 16, 18 can be determined by applying the formula for the circumference of a circle, and then dividing the result by 4 (i.e ¼ of the resulting value for each quarter circle). The formula and application are as follows:

$$\text{ConeLength}^2 = \frac{2\pi^*}{4}\text{mm} = \frac{\pi^*}{2}\text{mm}$$

*Assume vertical base and horizontal base lengths respectively=1 mm

As can be understood from FIGS. 4 and 5 and the formulae described above, the present balloon will have a ends which provide longer length in the inflated state then compared to a balloon having cone shaped ends oriented at 45 degree angles where both balloons have equivalent base lengths. The longer length of balloon ends 16, 18 when in the inflated state, provides the present inventive stent delivery system with the capability to draw a stent completely away from a pair of stent retaining sleeves disposed about the margins of the stent as described in detail below. As a result the present stent delivery system can deliver a stent with improved safety and consistency.

Balloon 14 may be composed of any thermoplastic polymer, or polymers, suitable for use as a medical balloon. Such thermoplastic polymers include, but are not limited to: polyethylene teraphtholate (PET), polybutylene teraphtholate (PBT), PEBAX™, Nylon™, polyurethane, polyester-polyether block copolymer such as ARNITEL™, polyolefin and polyolefin compounds. In addition, the present balloon may be manufactured by any means appropriate for manufacture a medical balloon. One such approach involves forming a balloon by stretching and blowing of the balloon from a segment of extruded polymer tubing. Another potential technique utilizes a balloon preform prepared by joining three segments of tubing end-to-end via the use of heat or adhesives. In the present case, proximal end 16, and distal end 18 could be joined to the body portion 20 in the manner described. When using such a process it may be possible to provide a balloon where, for instance, the ends are made from a first polymer material, and the body portion made from a second polymer material. Other combinations may be possible.

The balloon may also be constructed through the well known process of extruding the balloon material into a preform and conventionally blowing the balloon. The balloon material may be extruded uniformly or may be extruded in sequential segments and subsequently bonded together. All of the methods for constructing the present balloon are discussed in detail in U.S. patent application Ser. No. 09/076252 the entire contents of which are hereby incorporated by reference.

Turning back to FIGS. 1 and 2, a stent is shown disposed about body portion 20. The stent may be self-expanding, such as a NITINOL shape memory stent, or it may be expandable by inflating inflatable portion 14. Stent 30 is further characterized as having margins or edges 32, 34. The margins of the stent may be of a predetermined length. Overlying each of the stent margins 32, 34 is a respective stent retaining sleeve 42, 44. In the present invention, the stent retaining sleeves are preferably composed of a thermoplastic polymer or polymers characterized as having elastomeric qualities, which may be different or of the same composition as the inflatable portion 14 as described above.

Each of the stent retaining sleeves have a catheter attachment portion 46, 48 and a margin retaining portion 52, 54. The catheter attachment portions 46, 48 may be attached to the catheter in a variety of manners. The catheter attachment portions and the catheter may be chemically bonded, heat sealed, welded (lap welded, butt welded, laser welded, etc.) or otherwise bonded together. Devices such as retaining collars or bands may also be disposed around the catheter attachment portions to hold them against the catheter shaft. Other methods of attaching stent retaining sleeves to a catheter as may be known to one of ordinary skill in the art may also be employed.

When the inflatable portion or balloon is in the non-inflated state the margin retaining portions 52, 54, of the stent retaining sleeves, extend from the catheter shaft and respectively overlie balloon ends 16 and 18 as well as stent margins 32 and 34 as shown in FIG. 1. When balloon 14 is inflated margin retaining portions 52, 54 are drawn away from stent margins 32, 34, as shown in FIG. 2. As a result of ends 16, 18 having a hemispherical shape, the cones will have a sufficient length to allow the margin retaining portions 52, 54 to be drawn well away from the stent margins 32, 34, thereby freeing the stent for delivery when balloon 14 is in the fully inflated state as may be seen in FIG. 2.

After the stent has been deployed, the stent retaining sleeves will assist in reducing the radial diameter of the inflatable portion. As seen in FIG. 3, once stent 30 has been deployed the balloon 14 is reduced in diameter by deflation or evacuation of the inflation fluid. In addition, the elastomeric nature of stent retaining sleeves 42, 44 causes the margin retaining portions 52, 54 to radially collapse rounded ends 16, 18 of balloon 14. The rounded shape of ends 16, 18 provides an increased area for margin retaining portions 52, 54 to press upon, thus providing the present invention with improved collapsibility than compared to a balloon having cone shaped ends and correspondingly shaped sleeves. As a result of the ends 16, 18 being further collapsed by margin retaining portions 52, 54, balloon 14 will have a profile of sufficiently reduced nature to allow the stent delivery system to be safely and effectively withdrawn from the stent, vessel and subsequent guiding catheter.

This completes the description of the preferred and alternate embodiments of the invention. Those skilled in the art may recognize other equivalents to the specific embodiment described herein which equivalents are intended to be encompassed by the claims attached hereto.

What is claimed is:

1. a stent delivery system comprising:
   a catheter;
   a medical balloon mounted on the catheter, the medical balloon having a non-inflated state and being inflatable to an inflated state, the medical balloon characterized as including:
   a proximal end,
   a body portion,
   a distal end,
   wherein the proximal end and the distal end are hemispherical in shape such that the proximal and distal balloon ends have a radius of curvature between the balloon end and the body portion;
   a stent disposed about at least the body portion of the medical balloon, the stent having a first margin and a second margin, and
   at least one stent retaining sleeve, the at least one stent retaining sleeve having a balloon engagement end and a catheter disposed end, the balloon engagement end of the at least one stent retaining sleeve overlying an end of the medical balloon and at least a portion of the balloon engagement end of the at least one stent retaining sleeve overlying the a margin of the stent on the medical balloon when the medical balloon is in the non-inflated state, the at least a portion of the balloon engagement end of the at least one stent retaining sleeve being withdrawn from a margin of the stent when the medical balloon is in the inflated state, the catheter disposed end of the at least one stent retaining sleeve being disposed upon the catheter.

2. The stent delivery system of claim 1 wherein the at least one stent retaining sleeve further comprises a distal retaining sleeve and a proximal retaining sleeve.

3. The stent delivery system of claim 2 wherein the stent retaining sleeves are composed of a thermoplastic polymer.

4. The stent delivery system of claim 3 wherein the stent retaining sleeves are elastomeric.

5. The stent delivery system of claim 4 wherein the stent retaining sleeves are constructed and arranged to radially collapse the ends of the medical balloon subsequent to releasing the stent and deflating the medical balloon.

6. The stent delivery system of claim 2 wherein the catheter disposed end of the at least one stent retaining sleeve is bonded to the catheter.

7. The stent delivery system of claim 2 wherein the catheter disposed end of the at least one stent retaining sleeve is welded to the catheter.

8. The stent delivery system of claim 2 wherein the balloon engagement end of the proximal sleeve and the balloon engagement end of the distal sleeve retain the stent on the medical balloon when the medical balloon is in the non-inflated state and release the stent when the medical balloon is in the inflated state.

9. The stent delivery system of claim 1 wherein the medical balloon has a composition which includes a thermoplastic polymer.

10. The stent delivery system of claim 1 wherein the proximal end and the distal end of the medical balloon have a greater length when in the inflated state than when in the non-inflated state.

11. A stent delivery system comprising:
   a catheter having an inflatable portion, the inflatable portion having ends which are hemispherical in shape such that the ends have a radius of curvature in an axial direction, and
   a pair of sleeves overlying the ends of the inflatable portion and shaped to correspond to the contour of the ends of the inflatable portion.

12. The stent delivery system of claim 11 further comprising a stent, the stent disposed about the inflatable portion, the stent having margins, the sleeves overlying the margins of the stent when the inflatable portion is in a non-inflated state, the stent being released from the sleeves when the inflatable portion is inflated to an inflated state.

13. A stent delivery balloon having a non-inflated state and an inflated state, the stent delivery balloon comprising: a first end, a second end, and a body portion located therebetween, the first end and the second end being hemispherical in shape in the expanded state.

* * * * *